United States Patent [19]

Mikkelsen

[11] Patent Number: Plant 5,868

[45] Date of Patent: Jan. 27, 1987

[54] IMPATIENS PLANT NAMED ENTERPRISE

[75] Inventor: James C. Mikkelsen, Ashtabula, Ohio

[73] Assignee: Mikkelsens, Inc., Ashtabula, Ohio

[21] Appl. No.: 663,677

[22] Filed: Oct. 19, 1984

[51] Int. Cl.[4] ..... A01H 5/00

[52] U.S. Cl. ..... Plt./68

[58] Field of Search ..... Plt./68

*Primary Examiner*—R. E. Bagwill

*Attorney, Agent, or Firm*—Schwartz, Jeffery, Schwaab, Mack, Blumenthal & Evans

[57] ABSTRACT

An impatiens plant named Enterprise, having intense pink flowers, large leaf size with distinct variegation, tolerance to moisture stress, and its vigorous self-branching bush growth habit, which makes it useful for pot and hanging basket use.

1 Drawing Figure

The present invention relates to a new and distinctive cultivar of New Guinea Impatiens plant, botanically known as impatiens, and known by the cultivar name Enterprise.

The new cultivar was developed by me in Ashtabula, Ohio, through controlled breeding by crossing Mikkelsen Seedling No. 80-333-6 (seed parent)×Mikkelsen Seedling No. 80-113-1 (pollen parent). Asexual reproduction by terminal or stem cuttings taken by me in Ashtabula, Ohio, has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Larger, more vigorous growing plant than Twilight, disclosed in my pending application, and Corona, disclosed in U.S. Plant Pat. No. 5,184, but similar in growth habit and size to Eclipse and Astro, disclosed in U.S. Plant Pat. Nos. 4,689 and 4,691, respectively.

2. Flower color is a unique intense pink, with the central throat being dark red. Flower color is deeper than Gemini, U.S. Plant Pat. No. 5,132, but not as lavender pink as Comet, disclosed in my pending application, and Corona.

3. Flowers have good keeping qualities and tend to nestle in the foliage as they mature, similar to the flowering of Astro and Corona.

4. The new cultivar is highly self-branching, with a vigorous bush-type growth form. The plant is taller but denser than Gemini, and is outstanding in pots and baskets.

5. Leaf color and variegation are similar to Gemini, lighter than Astro and Eclipse, and darker than Comet. Enterprise has a red midrib and veins which are contrasted by the golden variegation.

6. Leaf size is large and lanceolate, similar to Gemini, with both cultivars having larger leaves than Corona, Astro and Eclipse.

7. Plants and flowers have good water stress abilities and can withstand more water stress without wilting than the other named cultivars. It also has good tolerance to low temperatures, growing and flowering after exposure to 2.2° C. after being planted out in early May.

8. Flowering begins earlier than Corona and Astro, but not as early as Comet, Solared (U.S. Plant Pat. No. 5,131), or Quasar.

9. Is an excellent cultivar to use for further hybridization in the development of cultivars that will withstand moisture stress without wilting.

The accompanying colored photograph taken in March 1984 illustrates the overall appearance in perspective view of Enterprise, and showing the colors as true as it is reasonably possible to obtain in a colored reproduction of this type.

The following is a detailed description of my new impatiens cultivar based on plants produced under commercial practices in Ashtabula, Ohio, grown in 5.5" green plastic pots during the winter of 1983–1984, and describes growth and flowering under adverse conditions. Color references are made to The Royal Horticultural Society Colour Chart except where general terms of ordinary dictionary significance are used.

Parentage: Mikkelsen Seedling No. 80-333-6×Mikkelsen Seedling No. 80-113-1.

Propagation:

(A) *Type cutting.*—Stem 15 mm long will develop 5 to 6 cm long in 18 to 21 days.

(B) *Time to root.*—8 to 10 days at 23° C. summer, 10–12 days at 20° C. winter.

(C) *Rooting habit.*—Large mass of fiberous roots from the stem.

Plant description:

(A) *Form.*—Symmetrical, bush shaped, flowering herb with a high degree of self-branching giving the plant a full appearance. Stems are reddish purple in color.

(B) *Habit of growth.*—Vigorous, self-branching, bush, continuous flowering.

(C) *Foliage description.*—Lanceolate deep green leaves which are quite large with moderate bronze variegation at the midrib. Veins are red. (1) size: 10 to 12 cm long and 3.75 to 4.25 cm wide on a mature leaf. (2) Shape: Lanceolate to ovate, acuminate apex with acute base. (3) Texture: Rugose upper side, glabrous under side. (4) Margin: Serrated, finely ciliated. (5) Color: Young foliage, top side 136A, under side 136B. Mature foliage, top side 131A, under side 183C. (6) Venation: Pinnate and red in color.

Flowering description:

(A) *Flowering habits.*—Flowers continuously from leaf whorl in progressive orderly manner, taking 5 to 7 days from buds which show color to bloom; flowers last 2 to 3 weeks.

(B) *Natural flowering season.*—Indeterminant and continuous. Quality of flowers increases with increasing levels of light intensity and duration.

(C) *Flower buds.*—Ellipsoidal, flowers perfect, reddish-purple spur 4.25 to 4.5 cm long on mature bud with throat behind ovary and originating from major sepal.

(D) *Flowers borne.*—On individual short pedicels from whorl of 5 to 7 leaves flowering progressively around the whorl as leaves and buds develop, and remaining just inside the leaf canopy.

(E) *Quantity of flowers.*—Floriferous, flowering continuously so that tight buds to mature blooms are visible at the same time in large numbers.

(F) *Petals.*—(1) Shape: Heart shaped, 2 wing petals smaller than other 3; gap between top petal and other 4 which overlap. (2) Color: Top side in winter when opening 68B, fading to 67D; blotched areas in the upper surface, when opening, 58B, with slight fading on maturity; the dark throat maintains the uniform color near 63A;

under side 64D, fading to 61D. (3) Number of petals: Five (5) in number. (4) Size of flowers: 6.5 to 7.5 cm.

(G) *Reproductive organs.*—(1) Stamens: Five (5) in number. (a) Anther shape: Hooded, color 68A. (b) Pollen color: Cream. (2) Pistels: (a) Stigma shape: Five (5) segmented column-shaped; pink in color. (b) Style color: Clear. (c) Ovaries: Five (5) in number, celled, size 4 mm until fertilized; greenish purple in color.

Disease resistance: No significant disease or insect problems have been seen to date.

I claim:

1. A new and distinct cultivar of New Guinea Impatiens plant named Enterprise, as described and illustrated, and particularly characterized by its intense pink flowers, large leaf size with distinct variegation, tolerance to moisture stress, and its vigorous self-branching bush growth habit, which makes it useful for pot and hanging basket use.

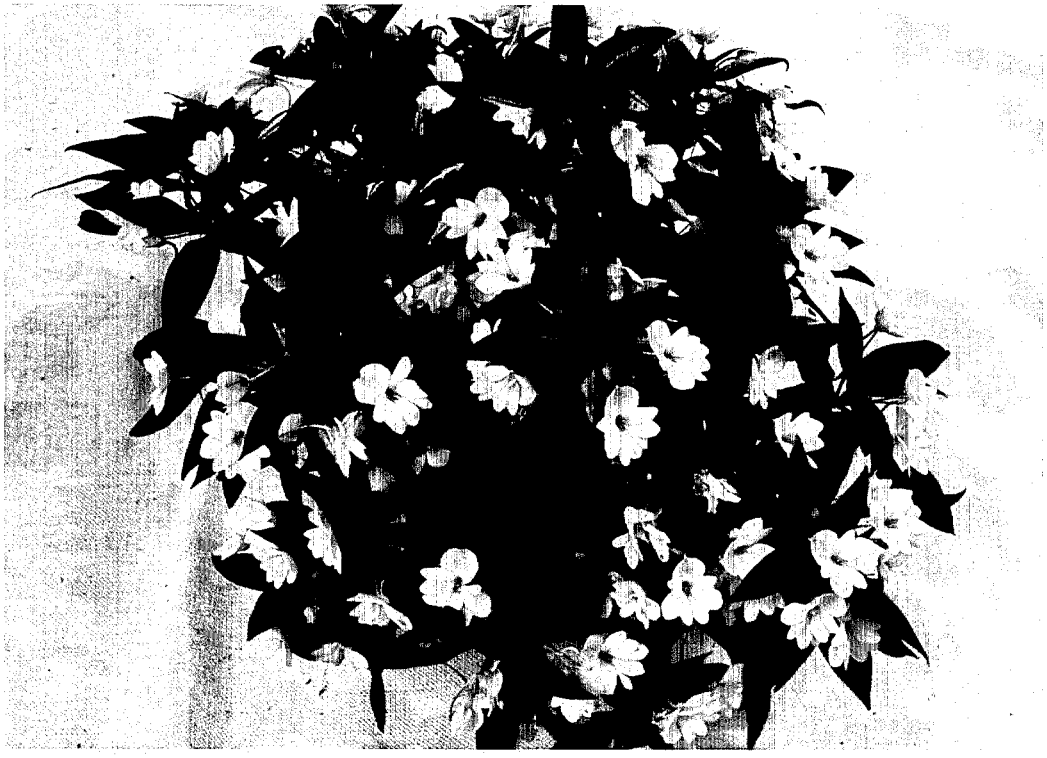

* * * * *